(12) United States Patent
Sarvis

(10) Patent No.: US 7,451,771 B2
(45) Date of Patent: *Nov. 18, 2008

(54) PORTABLE POUCH CLEANER

(76) Inventor: Edward J. Sarvis, 389 Halberta Cir., Calimesa, CA (US) 92320

( * ) Notice: Subject to any disclaimer, the term of this patent is extended or adjusted under 35 U.S.C. 154(b) by 351 days.

This patent is subject to a terminal disclaimer.

(21) Appl. No.: 11/307,757

(22) Filed: Feb. 21, 2006

(65) Prior Publication Data
US 2008/0004579 A1 Jan. 3, 2008

(51) Int. Cl.
*B08B 3/04* (2006.01)
(52) U.S. Cl. .................... 134/104.2; 604/332
(58) Field of Classification Search .............. None
See application file for complete search history.

(56) References Cited

U.S. PATENT DOCUMENTS

| | | | |
|---|---|---|---|
| 4,194,506 A | 3/1980 | Voorhies et al. | |
| 4,285,076 A * | 8/1981 | Dickstein ................ | 4/341 |
| 4,941,878 A | 7/1990 | Petrik et al. | |
| 5,503,633 A * | 4/1996 | Saunders et al. ............ | 604/332 |
| 5,709,236 A | 1/1998 | Rodriguez et al. | |
| 5,738,668 A | 4/1998 | Bugajski et al. | |
| 6,224,581 B1 * | 5/2001 | Withers et al. .............. | 604/334 |
| 6,532,971 B2 | 3/2003 | Deecki et al. | |

* cited by examiner

*Primary Examiner*—Mikhail Kornakov
*Assistant Examiner*—Eric Golightly
(74) *Attorney, Agent, or Firm*—Michael L. Greenberg, Esq.; Greenberg & Lieberman, LLC

(57) ABSTRACT

A device for cleaning an ostomy pouch is provided. The device comprises a waste collector having a wide mouth and a circular aperture in its base, a waste tube, a pedestal and first and second water sprayers connected to a high pressure water source. An ostomy pouch is hung from the mouth of the waste collector so that its contents are drained out into the waste collector from its closable drain end, while the other distant end of the pouch is attached to a user's stoma. One end of the waste tube is coupled to the aperture in the base of the waste collector while the other end is coupled to the pedestal. The pedestal is fitted onto a waste dispenser. Two water sprayers clean the waste collector and the colostomy pouch by washing the contents into the waste dispenser. The device is portable.

1 Claim, 2 Drawing Sheets

PORTABLE POUCH CLEANER

FIELD OF THE INVENTION

The present invention relates to cleaning of pouches or bags which become contaminated with human waste. More particularly, the present invention relates to a device and a method for cleaning colostomy bags and pouches.

BACKGROUND OF THE INVENTION

Some surgical procedures provide substitute paths for elimination of body wastes. This is necessitated by the removal or mal functioning of the gastrointestinal or urinary tract. Examples of such surgeries involving the intestinal tract include colostomy and ileostomy.

The bowel waste and other effluent are diverted through the colon to the surface of the abdomen. An opening or orifice is created in the abdomen for the elimination of the human waste there from. This surgically-created opening or "stoma" is coupled to a flexible waste collecting bag or pouch having an opening communicating therewith. The human waste is collected in the pouch. Periodically, the pouch is detached from the opening in order to eliminate the waste contents. Alternatively, the waste content is eliminated from the pouch using a closable drain end of the pouch, distant from the end connected to the stoma.

Such surgical procedures which result in the creation of an orifice in the body for waste elimination are generally referred to as ostomies and the waste collection pouches are generally called ostomy pouches. Thus, for example, the pouch used by a colostomy patient is typically referred to as a colostomy pouch. The ostomy pouches are generally made of durable high grade rubber or plastic and are, therefore, designed for repeated use. Therefore, the pouches require to be thoroughly cleaned before they can be used again after eliminating the waste contents.

Numerous types of cleaning devices are known in the art for cleaning colostomy pouches and the like. For example, U.S. Pat. No. 5,709,236, issued Jan. 20, 1998 to Rodriguez et al., describes a colostomy pouch rinsing device which utilizes a spray head attached to a tube. Water is supplied to the tube through a rubber hose which is connected to a faucet. A water control handle is provided which allows the user to control the flow of water to the spray head. In operation, the spray head is inserted into the colostomy pouch while a user holds the pouch over a toilet. The user manually holding the pouch during the washing procedure is not entirely satisfactory. In addition, it is easy for sprayed water to contact the user during the spraying procedure and the water and waste material exiting through the lower portion of the bag is prone to splashing in the toilet and can, therefore, contact the user. In order to prevent the splashing the user would be required to bend or kneel in front of the toilet, or else straddle the toilet. These are very uncomfortable postures, especially, for users having undergone a surgery. Since the cleaning process has to be repeated multiple times in a day, such postures can cause great discomfort to the users.

The ostomy pouch flusher described in U.S. Pat. No. 4,941,878, issued Jul. 17, 1990 to Petrik et al., uses a wand or tube which is inserted into a colostomy pouch so that water can be sprayed into the interior portion of the pouch during the cleaning operation. This device suffers from the same disadvantages described above.

U.S. Pat. No. 5,738,668, issued Apr. 14, 1998 to Bugajski et al., also describes a colostomy bag cleaning device which requires manually holding the bag and inserting a spray tube therein. This device, like the devices described above, requires the patient to insert the spray tube into the colostomy pouch while holding the pouch over the toilet. Thus, this device suffers from the same disadvantages noted above.

U.S. Pat. No. 4,194,506, issued Mar. 25, 1980 to Voorhies et al., discloses a kit for an ostomate. The kit includes a colostomy pouch consisting of a flexible, vertically elongated member with a closed top end for attachment to the stoma, with a downwardly open bottom end that can be opened for flushing, together with a directional water flushing appliance. Since the directional water flushing appliance is manually operated, it suffers from the same disadvantages as described above. In addition, this cleaning method can be applied only to the special colostomy pouch included in the kit and is not extendable to all colostomy pouches.

U.S. Pat. No. 6,532,971, issued Mar. 18, 2003 to Deecki et al., describes a device for cleaning the interior and exterior of a colostomy pouch. The pouch is required to be placed in a spray shield, which is then inserted in a toilet. The device includes a middle water sprayer for cleaning the interior of the pouch and two lateral water sprayers for cleaning the exterior of the pouch. Generally a colostomy pouch needs to be cleaned at least 4-5 times a day. Therefore, cleaning the pouch both from the interior and the exterior is a time consuming procedure, as this would also require drying the exterior of the pouch, before it can be used again.

In light of the above, despite the attempts made by the prior art devices, there still exists a need for an improved colostomy pouch cleaning device which allows quick yet sanitary cleaning of a colostomy pouch, while causing minimum discomfort to a user. None of the prior art patents, taken alone or in combination, teaches or suggests the presently claimed colostomy pouch cleaning device. Additionally, the pouch needs to be portable so that it can be used in hospitals for patients who are bedridden.

SUMMARY OF THE PRESENT INVENTION

The present invention provides a device for cleaning an ostomy pouch. The device comprises a waste collector having a wide mouth and a circular aperture in its base, a waste tube, a pedestal and, first and second water sprayers connected to a high pressure water source. An ostomy pouch, such as a colostomy pouch, is hung from the mouth of the waste collector so that its contents are drained out into the waste collector from its closable drain end, while the other distant end of the pouch is attached to a user's stoma. One end of the waste tube is coupled to the aperture in the base of the waste collector while the other end is coupled to the pedestal. The pedestal is fitted onto a waste dispenser. The first water sprayer cleans the waste collector by washing away the contents of the waste collector into the waste dispenser, through the waste tube. The second water sprayer being a straight tube with multiple holes drilled on its sides cleans the colostomy pouch by washing away the contents of the pouch into the waste dispenser, through the waste collector and the waste tube. Therefore, the pouch cleaning device described in the present invention facilitates the cleaning of a colostomy pouch sanitarily, without requiring a user to bend over, kneel down or straddle the waste dispenser.

Accordingly, a first objective of the invention is to provide a device for cleaning colostomy bags and the like which facilitates the cleaning in a posture comfortable to a user.

A second objective of the invention is to provide a device for cleaning a colostomy pouch or the like which allows sanitary cleaning of the pouch without requiring the user to contact the interior of the pouch during the cleaning operation.

A third objective of the invention is to provide a device for cleaning a colostomy pouch or the like with water sprayers emanating water under high pressure while protecting the user from spray and the contents of the pouch during the cleaning procedure.

A fourth objective of the invention is to provide a device for cleaning a colostomy pouch or the like which provides for the safe and effective cleaning of both the interior of the pouch and a user's stoma simultaneously, if the pouch is attached to the stoma with water proof seals.

A fifth objective of the invention is to provide a device for cleaning a colostomy pouch or the like which further provides for the delivery of waste and water from the cleaning procedure directly to a waste dispenser such as a toilet bowl while protecting the user from contact with the waste and the water.

A sixth objective of the invention is to provide a device that is readily portable so that the user can transport the device from one place to another if necessary. The device must be portable so that it can also be used for bedridden patients in hospitals.

These and other objects of the present invention will become readily apparent upon further review of the following specification and drawings.

BRIEF DESCRIPTION OF THE DRAWINGS

A more complete appreciation of the invention, and many of the attendant advantages hereof, readily will be apparent as same becomes better understood by reference to the following detailed description when considered in conjunction with the accompanying drawings in which like reference symbols indicate the same or similar components, wherein.

DETAILED DESCRIPTION OF THE PREFERRED EMBODIMENTS

Figure 1:
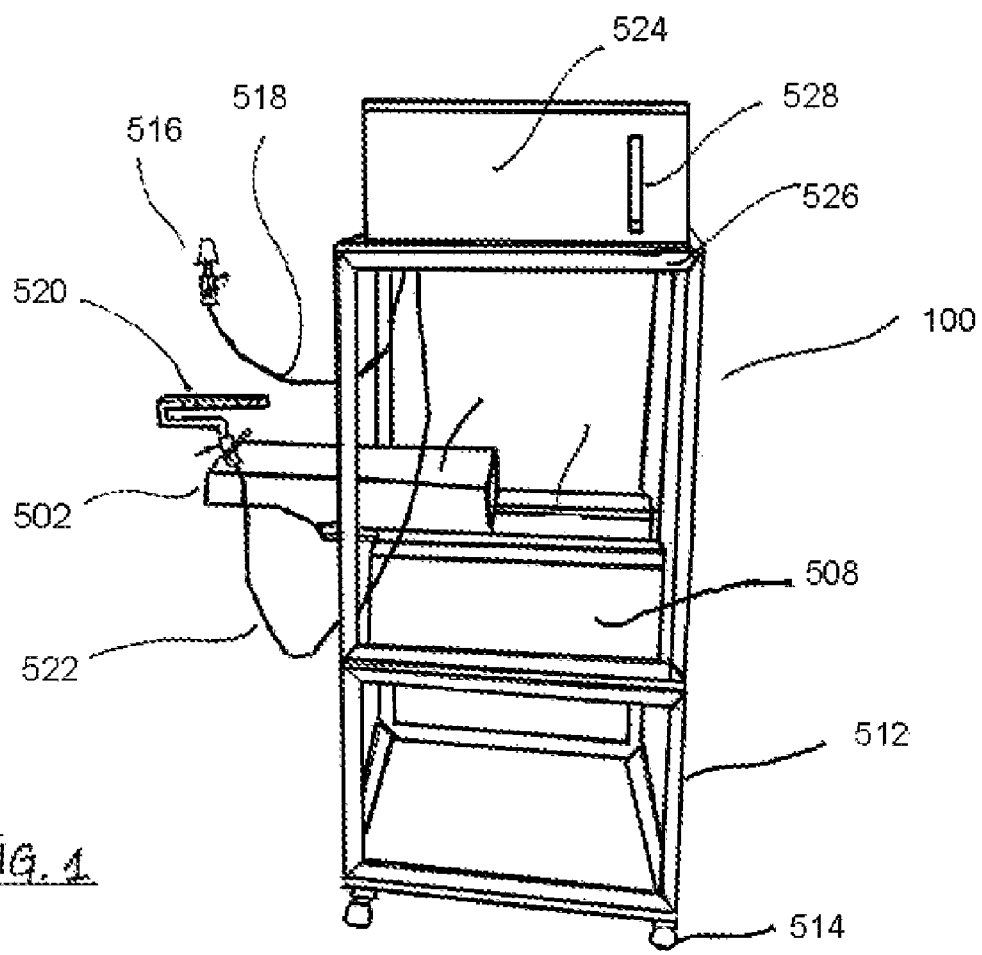
FIG. 1 shows an environmental view of the present invention.

FIG. 1 illustrates a pouch cleaning device (100), in accordance with an embodiment of the present invention. The pouch cleaning device (100) is used to hygienically and conveniently dispense the contents of an ostomy pouch or bag, such as a colostomy pouch. A typical colostomy pouch is sealed around a surgically created orifice, called stoma, in a user's abdomen. One end of the colostomy pouch, which is sealed around the stoma, receives the user's body waste, while the other distant end can be opened to drain out the collected waste contents of the pouch. The pouch is cleaned by washing it from the inside after draining away its contents. The cleaning can be performed either after removing the colostomy pouch from the stoma, or while it is still attached to the stoma. In an embodiment of the invention, the pouch cleaning device (100) cleans the colostomy pouch while it is attached to a user's stoma.

Figure 1B:
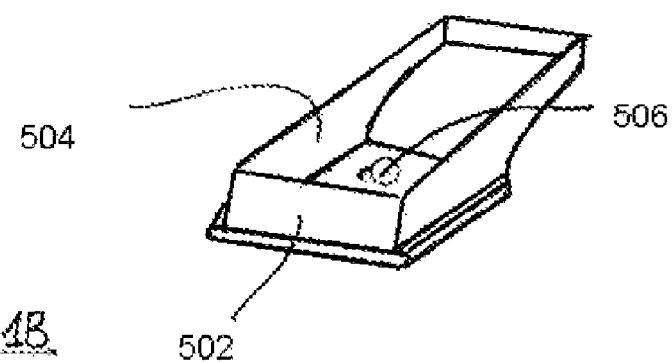
FIG. 1B shows an exploded environmental view of the waste container of the present invention.

FIG. 1 illustrates a portable pouch cleaning device (100) in accordance with an embodiment of the invention. The pouch cleaning device (100) is a portable device that enables patients lying on a bed, such as a hospital bed, to conveniently use the device for cleaning their colostomy pouches. As shown in FIG. 1B the portable device (100) comprises a bedpan (502) having a first aperture (504) and a distant second aperture (506). The second aperture (506) is smaller than the first aperture. The bedpan (502) receives the contents of the ostomy pouch through the first aperture (504) and the second aperture (506) passes the washed contents of the bedpan (502) and the ostomy pouch therefrom. In an embodiment of the invention, the bedpan (502) has a hole drilled in the bottom, such that the contents of the ostomy pouch are emptied into the bedpan (502) and pass through the hole into a waste collector (508) which receives the washed contents of the bedpan (502) and the ostomy pouch. The bed pan (502) is contoured such that when in use it fits over a user's body part such as the user's thighs. The bedpan (502) is fitted onto the waste collector (508) by means of a slider mechanism (510), such as sliding rails. The slider mechanism (510) enables the bedpan (502) to move slidingly on the waste collector (508). The waste collector (508) is mounted on a movable stand (512) provided with wheels (514). In an embodiment of the present invention, the height of the stand (512) is such that when in use, the stand (512) is wheeled adjacent an end of the bed and the bedpan (502) is slid out over the bed, enabling a user to empty the contents of the ostomy pouch, attached to the user's body, into the bedpan (502), while sitting in an upright position on the bed. After use the bedpan (502) is slid back onto the waste collector (508) away from the bed.

The portable device (100) further comprises a first water sprayer (516) for cleaning the bedpan (502) by washing away the contents of the bedpan (502) through the second aperture (506) into the waste collector (508). The first water sprayer (516) is coupled to a first conduit (518) which passes water to the first water sprayer (516). A second water sprayer (520) is provided for cleaning the ostomy pouch by washing away the contents of the ostomy pouch through the second aperture (506) into the bedpan (502), the second water sprayer (520) is coupled to a second conduit (522) which passes water to the second water sprayer (520). The second water sprayer (520) is a straight tube comprising a plurality of holes on the sides. The first conduit (518) and the second conduit (522) draw water from a water tank (524). The water tank is fitted onto a frame (526) mounted on the stand (512) and is placed at a level higher than a level of the waste container (508) so that the water can flow through the conduits into the first and the second water sprayers (516), (520).

In an embodiment of the present invention, the water tank (524) is manually filled and the level of water in the water tank (524) is indicated through a clear water indicator (528). Both the first and the second conduits (518), (522) comprise a flexible hose and a manually operable valve for controlling the passage of water to the first and the second water sprayers (516), (520) respectively. The second conduit (522) is coupled to the second water sprayer (520) via a connector comprising an assembly of tubes and elbow connectors, the connector being configured to place the second water sprayer in an upright position in the waste collector.

Figure 2:
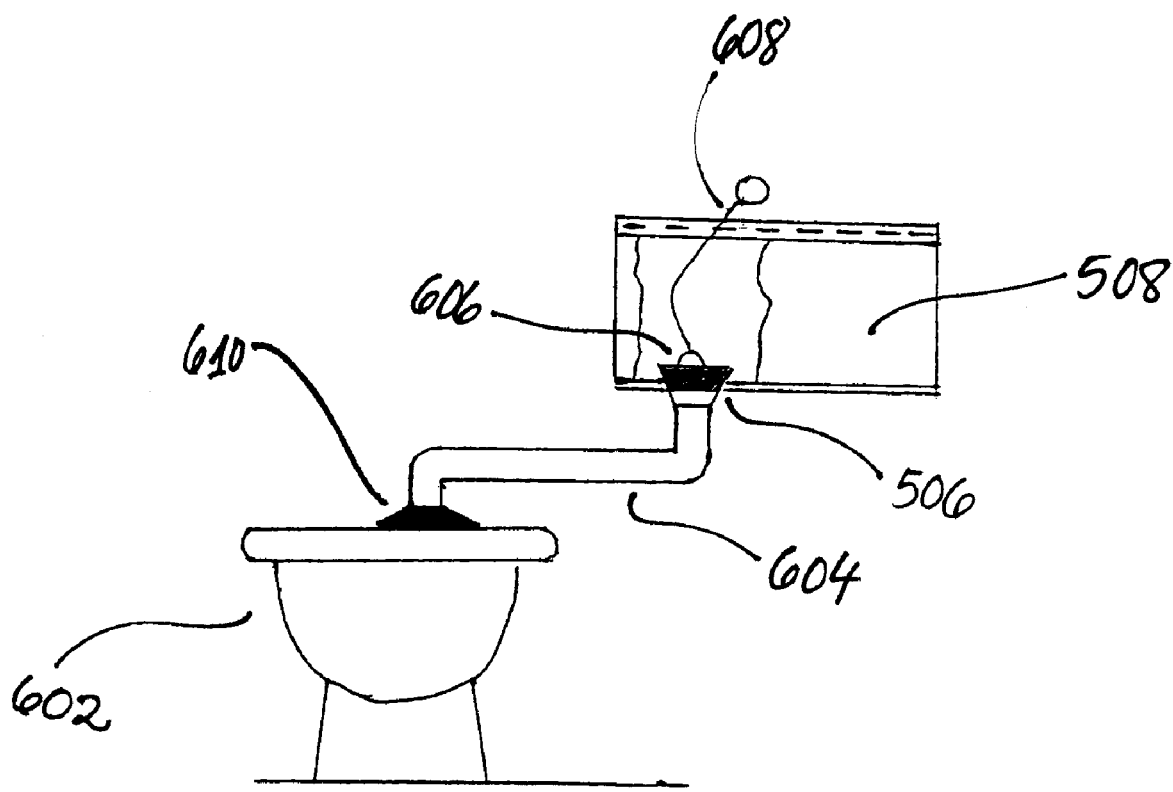
FIG. 2 shows a splash guard and waste tube of the present invention.

FIG. 1B illustrates an exploded view of the bedpan (502) with apertures (504) and (508), in accordance with an embodiment of the invention. In an embodiment of the present invention, the waste collector (508) is a rectangular container removable from the stand. As shown in FIG. 2, the waste collector (508) is manually emptied into an American standard toilet bowl via a waste tube (604). The waste collector (508) is provided with an aperture (506) in the bottom through which it couples with the waste tube (604) and can swivel to preferably 100 degrees. Preferably the waste collector (508) is 20 inches wide, 8 inches tall and 22 inches long and has tracks for the bedpan (502) so that the bedpan (502) can slide. The aperture (506) is plugged using a stopper (606) provided with a pull chain (608), when the waste collector (508) is receiving the contents of the bedpan (502). When the contents of the waste collector (508) are being emptied it is unplugged by pulling the pull chain (608), thereby causing the contents to flow into the toilet (602) via the waste tube (604).

A splash guard (610), is shown in FIG. 2 so that when the waste tube (604) dumps waste into the toilet (602), the waste does not splash all over the interior of the toilet (602). Splash guard (610) is attached to waste tube (604) via any conventional means, such as via a conventional collar that would hold splash guard (610) to the bottom of waste tube (604).

Preferably all tanks and the bedpan (502) as well as the tubular frame (512) are made of stainless steel. The unit (100) fits easily through standard doors. The portable unit (100) can be wheeled to any bed bound patient. The bedpan (502) slides towards and away from bed via any conventional means but can never leave the track (510) in a forward position meaning there is little chance of the bedpan (502) falling out of the frame (512). The frame (512) can accommodate any adjustable hospital bed. The tank (524) preferably has a capacity of 12 gallons.

While the present invention has been described in terms of certain preferred embodiments, one skilled in the art will readily appreciate that various modifications, changes, omissions and substitutions may be made without departing from the spirit thereof. It is intended, therefore, that the present invention be any and all embodiments with the scope of the following claims.

What is claimed is:

1. A device for cleaning an ostomy pouch, the device comprising:

a bedpan having a first aperture and a distant second aperture, the second aperture being smaller than the first aperture, the bedpan receiving the contents of the ostomy pouch through the first aperture;

a waste tube coupled to the second aperture of the bedpan, the waste tube passing washed contents of the bedpan and the ostomy pouch to a waste collector;

a portable frame carrying said bedpan and said waste collector;

a first water sprayer for cleaning the waste collector by washing away the contents of the waste collector through the waste tube into a waste dispenser, the first water sprayer being coupled to a first conduit passing water therefrom;

a second water sprayer for cleaning the ostomy pouch by washing away the contents of the ostomy pouch through the waste tube into the waste dispenser, the second water sprayer being connected to a second conduit passing water therefrom, the second water sprayer comprising a plurality of holes on sides of a straight tube;

a coupler connected to the first and the second conduit for connecting the conduits to a source of water so that the water can flow through the conduits into the first and the second water sprayers; and wherein said portable frame comprises a large square frame coupled to a small square frame using a plurality of angled legs, the square frames comprising a plurality of straight pipes, elbow joints and t-joints.

\* \* \* \* \*